United States Patent [19]
Ueda et al.

[11] Patent Number: 5,235,071
[45] Date of Patent: Aug. 10, 1993

[54] CATALYST FOR PRODUCING PHTHALIC ANHYDRIDE AND PROCESS BY USING THE SAME

[75] Inventors: Kenji Ueda; Masaaki Okuno; Tatsuya Kawabata; Shinya Tanaka, all of Hyogo, Japan

[73] Assignee: Nippon Shokubai Co., Ltd., Osaka, Japan

[21] Appl. No.: 906,717

[22] Filed: Jun. 30, 1992

[30] Foreign Application Priority Data

Jul. 10, 1991 [JP] Japan .................. 3-169622

[51] Int. Cl.$^5$ .................. B01J 27/14; B01J 27/20; C07D 307/89
[52] U.S. Cl. .................. 549/248; 549/256; 549/257; 549/258; 549/259; 549/260; 549/249; 502/113; 502/114; 502/179; 502/120; 502/209
[58] Field of Search .............. 549/248, 256, 257-260, 549/249; 502/179, 113, 114, 120, 209

[56] References Cited

U.S. PATENT DOCUMENTS

| | | | |
|---|---|---|---|
| 3,843,552 | 10/1974 | Jouy et al. | 549/248 |
| 3,909,457 | 9/1975 | Friedrichsen et al. | 549/248 |
| 3,926,846 | 12/1975 | Ono et al. | 252/435 |
| 4,046,780 | 9/1977 | Nakanishi et al. | 504/204 |
| 4,284,571 | 8/1981 | Sato et al. | 252/435 |
| 4,356,112 | 10/1982 | Nakanishi et al. | 549/248 |
| 4,436,922 | 3/1984 | Kita et al. | 549/251 |
| 4,481,304 | 11/1984 | Sato et al. | 502/209 |

FOREIGN PATENT DOCUMENTS

| | | |
|---|---|---|
| 47-5661 | 3/1972 | Japan . |
| 47-15323 | 5/1972 | Japan . |
| 49-41036 | 4/1974 | Japan . |
| 49-89694 | 8/1974 | Japan . |
| 57-105241 | 6/1982 | Japan . |
| 59-1378 | 1/1984 | Japan . |
| 1203321 | 8/1970 | United Kingdom . |

*Primary Examiner*—Cecilia Tsang
*Attorney, Agent, or Firm*—Lowe, Price, LeBlanc & Becker

[57] ABSTRACT

The invention relates to a catalyst for producing phthalic anhydride by gas phase catalytic oxidation of o-xylene and/or naphthalene with molecular oxygen or gas containing molecular oxygen and, to a process for producing phthalic anhydride by using said catalyst. The catalyst is made by supporting, on a heat-resistant inorganic carrier, a catalytic active substance which comprises: vanadium oxide; anatase type titanium dioxide having specific surface area of 10 to 60 $m^2/g$; niobium; at least one element selected from potassium, cesium, rubidium and thallium; phosphorus; and antimony. The catalytic active substance is prepared by using a five-valent antimony compound as an antimony source. The process for producing phthalic anhydride comprises use of said catalyst.

5 Claims, 5 Drawing Sheets

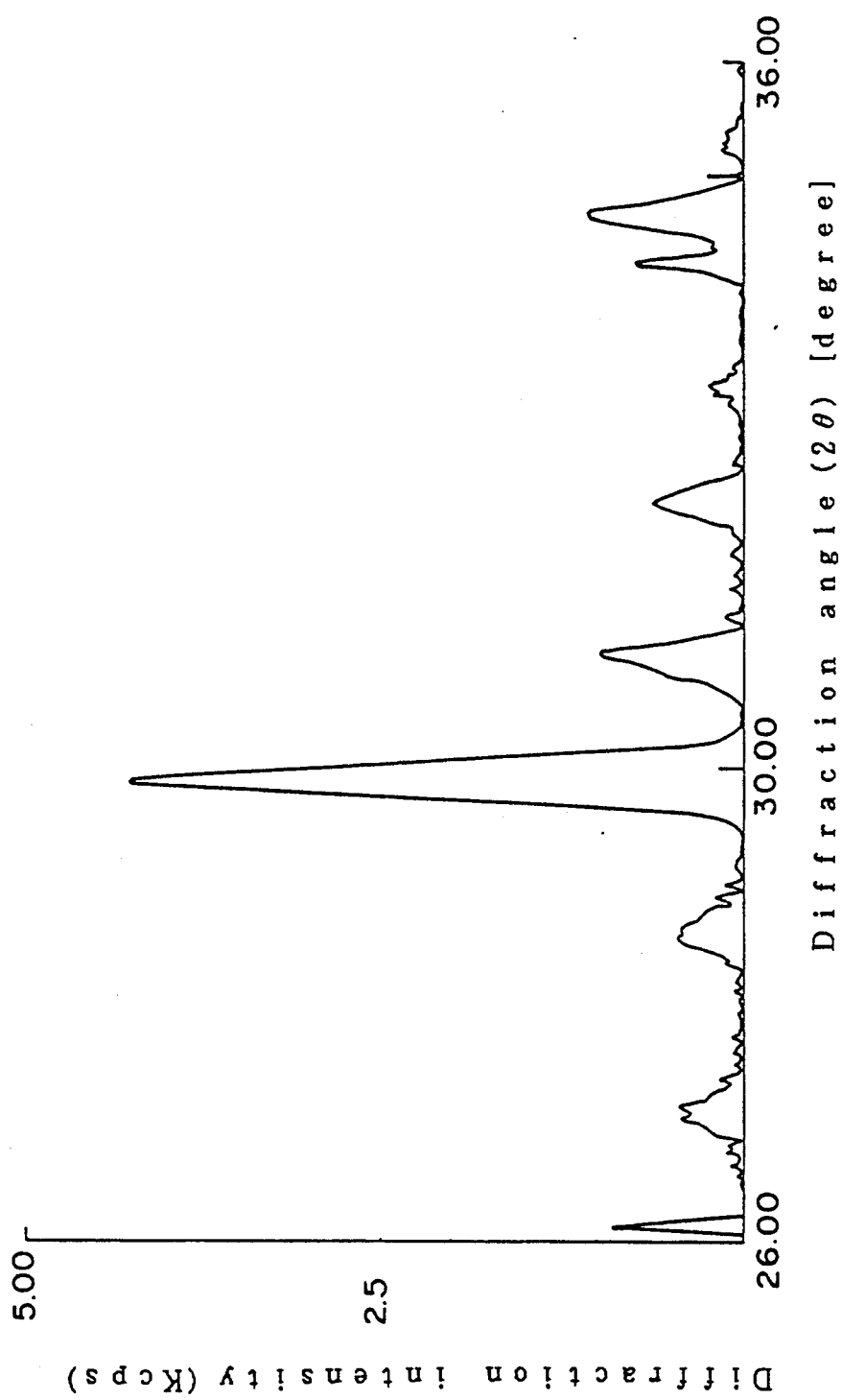

CATALYST FOR PRODUCING PHTHALIC ANHYDRIDE AND PROCESS BY USING THE SAME

BACKGROUND OF THE INVENTION

The present invention relates to a catalyst for producing phthalic anhydride and a process for producing it by using the same and, in detail, it relates to a catalyst for producing phthalic anhydride by vapor phase catalytic oxidation of o-xylene and/or naphthalene with molecular oxygen or gas containing molecular oxygen and, to a process for producing phthalic anhydride by using the catalyst.

In recent years, when phthalic anhydride is produced by vapor phase catalytic oxidation of o-xylene and/or naphthalene with molecular oxygen or gas containing molecular oxygen, an increase in the yield is attempted, after obtaining a crude product at first, by treating it with heat and subjecting it to distillation. Since this process is simple and facile to perform, there can be expected a significant effect such that a product of high quality is produced in a large scale with a cheap price.

Furthermore, as a means to elevate the yield, there is a process comprising stabilized production resulting from maintaining reaction conditions and catalytic activity. An example of this process is an oxidation reaction carried out under high load reaction conditions such as high concentration of a starting material gas. However, production of phthalic anhydride from o-xylene or naphthalene is accompanied by violent heat generation and, under high concentration conditions, temperature rise at a hot spot part is extreme, so that excessive oxidation occurs, the yield of phthalic anhydride is lowered, and deterioration of the catalyst is extremely accelerated. Catalysts capable of withstanding such high load reaction conditions have been already proposed, for example, in U.S. Pat. No. 4,356,112.

A widely known catalyst of this kind is a catalyst for producing phthalic anhydride, having supported on an inactive carrier a catalytic active substance containing vanadium oxide and titanium oxide as main components. Catalysts of the type are disclosed, for example, in G.B. 1,203,321, U.S. Pat. No. 4,046,780, Japanese Examined Patent Publication of showa 49-41036, U.S. Pat. No. 3,843,552, U.S. Pat. No. 3,909,457, and Japanese Unexamined Patent Publication of showa 57-105241. These catalysts have their respective features and some of them have been proved as useful by being applied for an industrial use.

There is, however, ample room for improvement of catalyst performance; an increase in yield of only 1% is notable in its economic effect considering the scale of production.

SUMMARY OF THE INVENTION

The present invention provides a catalyst further improved on the catalyst performance compared with hitherto-known conventional catalysts and, therefore, useful for producing phthalic anhydride.

Accordingly, it is an object of this invention to provide a catalyst for producing phthalic anhydride with high selectivity by vapor phase catalytic oxidation of o-xylene and/or naphthalene.

It is a further object of this invention to provide a catalyst for producing phthalic anhydride by vapor phase catalytic oxidation of o-xylene and/or naphthalene, which makes it possible to produce phthalic anhydride with high selectivity even under high load and high temperature conditions and, which is superior in durability and makes it possible to produce phthalic anhydride under stable conditions for a long period of time.

The present inventors have found by extensive research that the above-mentioned object is attained, especially under a high temperature condition, by using a five-valent antimony compound such as represented by $Sb_2O_5$ as a starting material, instead of a conventional trivalent antimony compound such as represented by $Sb_2O_3$, in introducing antimony into a vanadium-titanium-based catalyst as an ingredient of catalytic active substances. Based on this finding, the present invention was achieved.

Furthermore, it is found that the above-mentioned object is attained, especially under a high temperature condition, by using a five-valent antimony compound such as represented by $Sb_2O_5$ as a starting material to introduce antimony even in a vanadium-titanium-based catalyst into which silver has been already added.

The first invention provides a catalyst for producing phthalic anhydride by vapor phase catalytic oxidation of o-xylene and/or naphthalene with molecular oxygen or gas containing molecular oxygen, having supported on a heat-resistant inorganic carrier a catalytic active substance;

which comprises (A) 1 to 20 parts by weight of vanadium oxide as $V_2O_5$, and 99 to 80 parts by weight of anatase type titanium dioxide with specific surface area of 10 to 60 $m^2/g$ as $TiO_2$; and (B), per 100 parts by total weight of (A), 0.01 to 1 part by weight of niobium as $Nb_2O_5$, 0.05 to 2 parts by weight of at least one element selected from potassium, cesium, rubidium and thallium as oxide, 0.2 to 1.2 parts by weight of phosphorus as $P_2O_5$, 0.55 to 5.5 parts by weight of antimony as $Sb_2O_5$; and wherein a five-valent antimony compound is used as an antimony source in production of the catalytic active substance.

Hereinafter, this obtained catalyst is referred to as catalyst 1.

The second invention provides a catalyst for producing phthalic anhydride by vapor phase catalytic oxidation of o-xylene and/or naphthalene with molecular oxygen or gas containing molecular oxygen, having supported on a heat resistant inorganic carrier a catalytic active substance;

which comprises (A) 1 to 20 parts by weight of vanadium oxide as $V_2O_5$, and 99 to 80 parts by weight of anatase-type titanium dioxide with specific surface area of 10 to 60 $m^2/g$ as $TiO_2$; and (B), per 100 parts by total weight of (A), 0.01 to 1 part by weight of niobium as $Nb_2O_5$, 0.05 to 2 parts by weight of at least one element selected from potassium, cesium, rubidium and thallium as oxide, 0.2 to 1.2 parts by weight of phosphorus as $P_2O_5$, 0.05 to 2 parts by weight of silver as $Ag_2O$, 0.55 to 5.5 parts by weight of a five-valent antimony compound as $Sb_2O_5$, and wherein a five-valent antimony compound is used as an antimony source in production of the catalytic active substance.

Hereinafter, this obtained catalyst is referred to as catalyst 2.

It is one of the features of the invention that anatase type titanium dioxide with specific surface area of 10 to 60 $m^2/g$, preferably 15 to 40 $m^2/g$, is used as an ingredient of the catalytic active substance. If the specific surface area of the anatase type titanium dioxide is less than 10 m²/g, the activity of the obtained catalyst is low; when it exceeds 60 m²/g, the durability of the catalyst is reduced and the yield rapidly decreases, which is not preferable (the specific surface area is measured by the BET method).

Although there are a so-called "solution method" and so-called "solidifying method" as methods for producing the anatase type titanium dioxide, the solution method is preferred for use.

According to the solution method, ilmenite (FeOTiO₂) is treated with aqueous sulfuric acid of about 70 to 80% concentration, hydrolyzed under pressure at about 150° C., and calcined to obtain anatase type titanium dioxide. The obtained anatase type titanium dioxide is high in mechanical strength in spite of porosity; it possesses such strength as to be regarded as "primary particles" not crushed by mechanical grinding by an ordinary ball mill or the like. Although this anatase type titanium dioxide has a large average particle size of 0.4 to 0.7 $\mu$m, it has such a large specific surface area as 10 to 60 m²/g, and it is essentially an assembly of primary particles of small diameter (the average particle size is measured by a transmission electron microscope). Among the particles, the ones having a sphere shape are preferred for practical use.

Furthermore, the solidifying method is somewhat inconvenient in practical use because this method is performed in sulfuric acid of higher concentration compared with the solution method.

Due to an ore used as a starting material, there is a case where iron, zinc, aluminum, manganese, chromium, calcium, lead and so forth mingle in the anatase type titanium dioxide, however, as far as they are 0.5% by weight or less as oxide against the titanium dioxide, there is no problem on the catalytic performance.

The heat-resistant inorganic carrier used in this invention is required to be stable for a long period of time at a temperature sufficiently higher than the catalyst-calcining temperature as well as at a temperature of the catalyst in producing phthalic anhydride and also, it is required to be unreactive with the catalytic active substance. Preferable examples of heat-resistant inorganic carriers of this kind are silicon carbide (SiC), alumina, zirconium oxide, titanium oxide and the like.

Among these carriers, the silicon carbide carrier is very preferable and, a preferable alumina (Al₂O₃) content in this silicon carbide is 20% by weight or less and its further preferable content is 5% by weight or less. A further preferable carrier is a silicon carbide carrier obtained by self-sintering of silicon carbide powder with a purity of 98% or more. A preferable apparent porosity of the silicon carbide carrier is 10% or more and a further preferable one is a range of from 15 to 45%.

The shape of the heat-resistant inorganic carrier is not particularly limited, but a spherical or columnare shapes are easy to handle and such a carrier as having an average diameter of 2 to 15 mm is preferable for use.

A feature of the catalyst relating to this invention is to use a five-valent antimony compound such as represented by Sb₂O₅ as an antimony source, that is one ingredient of the catalytic active substance, and the antimony compound is properly selected from various kinds of five-valent antimony-containing compounds in addition to the Sb₂O₅. An amount for use of the antimony compound is 0.55 to 5.5 parts by weight as Sb₂O₅ per 100 parts by weight of the sum of the two ingredients, that are vanadium oxide and anatase type titanium dioxide: a preferably amount for use is 1.5 to 3.5 parts by weight as Sb₂O₅. If the content of antimony is too much or too small, the object of this invention is not attained.

Preferable five-valent antimony-containing compounds are such as having an average particle size in a range of from 1 to 40 $\mu$m and further preferable ones are such as having the size in a range of from 5 to 30 $\mu$m. If the average particle size is larger than 40 $\mu$m, activity deviation becomes large in converting the five-valent antimony-containing compound into a catalyst with other ingredients. That is due to difficulty in keeping the most suitable temperature at constant. This may arises from uneven distribution of antimony particles in the catalyst-active layer. Also, if the average particle size is smaller than 1 $\mu$m, the catalyst activity becomes higher than a case where particles having an average particle size of 1 $\mu$m or larger and also, the effect of adding five-valent antimony becomes low. This may be because the reaction activity on the surface of the five-valent antimony-containing compound itself is high. (The average particle size is determined by a transmission electron microscope before preparing the catalyst.)

The vanadium, niobium, potassium, cesium, rubidium, thallium and phosphorus starting materials for preparing the catalyst may be selected from, aside from such oxides as V₂O₅, Nb₂O₅, K₂O, Cs₂O, Rb₂O, Tl₂O and P₂O₅, compounds transformed to such oxides by heating such as ammonium salts, nitrates, sulfates, halides, organic acid salts and hydroxides of the individual elements.

A preferable total amount for use of the potassium, cesium, rubidium and thallium is, per 100 parts by total weight of vanadium oxide and anatase type titanium dioxide, 0.05 to 2 parts by weight as the forementioned respective oxides, and a preferable amount for use of phosphorus and niobium is 0.2 to 1.2 parts by weight as P₂O₅ and 0.01 to 1 part by weight as Nb₂O₅, respectively. If the content is too much or too small, the object of this invention is not attained.

Concerning the catalyst 2 relating to the present invention, silver is one additional ingredient, aside from the catalytic active substances shown in the catalyst 1.

As for the silver ingredient, aside from Ag₂O, a nitrate, halide, an ammonium salt, organic acid salt, a hydroxide, an amine complex, a phosphate, sulfide and the like may be used. Some of them, such as silver halide and silver phosphate, are not transformed into oxide by heating in the production of the catalyst, but all of them may be used in this invention without trouble.

A preferable amount for use of silver is, per 100 parts by total weight of vanadium oxide and anatase type titanium dioxide, 0.05 to 2 parts by weight as Ag₂O. If the content is too much or too small, the object of this invention is not attained.

In a case where silver phosphate is used, because this compound consists of phosphorus and silver and does not contribute as a phosphorus additive, the phosphorus in silver phosphate is not included in the forementioned phosphorus content of 0.2 to 1.2 parts by weight as P₂O₅.

Although the amount of a catalytic active substance to be supported on the heat-resistant inorganic carrier varies with the carrier size, and a preferable amount is 3 to 20 g per 100 cc of the carrier. The catalytic active substance layer obtained by supporting the catalytic active substance on the carrier has preferably a surface such that the pore volume occupied by pores of 0.15 to 0.45 $\mu$m diameter is 50% or more (preferably) 75% or more, of the total fine pore volume occupied by pores of 10 μm or less diameter (the pore volume is obtained from a pore-diameter distribution measured by a mercury injection porosimeter). The object of this invention is more effectively attained by arranging a catalytic active substance layer having such surface characteristics as mentioned above.

The method of supporting the catalytic active substance on a heat-resistant inorganic carrier in production of catalysts of this invention is not particularly limited, and various known methods can be used. The most simple method is to put a specific amount of carrier into a rotary drum which can be heated from outside and, while keeping it at a temperature of 200° to 300° C., to spray a slurry containing the catalytic active substance on the carrier to support the substance.

A practical method of arranging a catalytic active substance layer having such surface characteristics as mentioned above is mentioned. When a slurry is prepared by using anatase type titanium dioxide with a primary particle size of 0.005 to 0.05 μm, the slurry concentration is adjusted at 5 to 25% by weight, preferably 10 to 20% by weight; and when using anatase type titanium dioxide with a primary particle size greater than 0.05 μm, the slurry concentration is adjusted at 10 to 40% by weight, preferably 15 to 25% by weight; and the slurry obtained is made sufficiently uniform by using an emulsifier, a heat-resistant inorganic carrier is placed into a rotary drum kept at a temperature of 200° to 300° C., the forementioned slurry is sprayed with rotating the drum so that a catalytic active substance can be supported in a defined content, and then a carrier which has supported the active substance is calcined in passing air at a temperature of 450° to 700° C., preferably 500° to 600° C., for about 2 to 10 hours to obtain a catalyst of this invention.

The oxidation reaction of o-xylene and/or naphthalene using a catalyst of this invention can be carried out under usual reaction conditions. For example, a reaction tube of inside diameter 5 to 40 mm, preferably 15 to 27 mm, is filled with the catalyst to a height of 1 to 5 m, preferably 1.5 to 3 m, and maintained at a temperature of 340° to 420° C., preferably 360° to 400° C., by a heating medium. Into this reaction tube, the o-xylene and/or naphthalene is blown, together with air or gas containing 5 to 21% by volume of molecular oxygen, at a rate of 5 to 70 g per $Nm^3$ of air or at a rate of 5 to 110 g per $Nm^3$ of gas containing molecular oxygen, at a spatial velocity of 1,000 to 6,000 $hr^{-1}$ (STP), preferably 1,000 to 4,000 $hr^{-1}$ (STP).

The third and fourth inventions relate to a process by which the catalysts 1 and 2 are used with great advantage. In the inventions, the catalyst layer in a reaction tube is divided into two or more sections to arrange a plurality of reaction zones, a plural piece of catalysts of controlled activity are charged in the reaction zones so that the catalytic activity is higher from the material gas inlet of the reaction tube toward the outlet. Preferably, the reaction tube is divided into two layers, and the inlet part is filled with a defined catalyst (first stage catalyst) to a layer height of 30 to 70% of the overall catalyst layer height, while the remaining layer height at the outlet is filled with catalyst (second stage catalyst) of higher activity than the first stage catalyst, and thus the catalysts are provided for the oxidation of o-xylene and/or naphthalene.

An example for preparing catalyst 2 of this invention is explained. Catalysts of the same type but different in activity may be easily prepared by changing the content of, for example, phosphorus. Thus, using 0.2 to 0.4 parts by weight of phosphorus as oxide in the catalytic active substances per 100 parts by total weight of the vanadium oxide and anatase type titanium dioxide, an above first stage catalyst is prepared, and using 0.4 to 1.2 parts by weight, a second stage catalyst of higher activity is prepared.

The catalyst activity may also be controlled by varying the kind and/or content of at least one element selected from potassium, cesium, rubidium and thallium.

Furthermore, a catalyst-filled layer of controlled activity may be made by a joint use of the catalyst 1 and catalyst 2.

By performing the oxidation reaction under such conditions as mentioned above, heat accumulation in the hot spot in the catalyst layer is suppressed and, as a result, catalyst deterioration due to thermal load is reduced, so that long-term stable operation is possible industrially. Excessive oxidation reaction at the hot spot is prevented and various effects are obtained, including improvement of the selectivity.

If a five-valent antimony-containing compound is used as a source of antimony which is an ingredient of the catalytic active substance, the most suitable reaction temperature of the catalyst at a final stage becomes higher than a case where a three-valent antimony-containing compound is used.

Such effects are particularly notable under high load reaction conditions such as high gas concentration of o-xylene and/or naphthalene, so that productivity can be very enhanced.

By using the catalyst of this invention, phthalic anhydride can be manufactured at high selectivity from o-xylene and/or naphthalene. The operations of heat treatment and distillation to obtain phthalic anhydride product are facilitated, and products of higher quality may be obtained at lower cost as compared with conventional methods.

The catalyst of this invention is durable, and accordingly long-term stable operation is possible industrially. Even under high load reaction conditions such as high concentration of material gas flow and even under high temperature conditions such as 380° C. or more, phthalic anhydride is produced with high selectivity, and even if the catalyst is used for a long period of time, it is durable and the productivity of phthalic anhydride is very much enhanced. Accordingly, the catalyst of the invention is extremely useful for producing phthalic anhydride.

BRIEF DESCRIPTION OF THE DRAWINGS

FIG. 5 is a chart showing the result from X-ray diffraction analysis of the catalyst E obtained from the example 2 in the region of a 26° to 36° diffraction angle.

DESCRIPTION OF THE PREFERRED EMBODIMENTS

Figure 1:
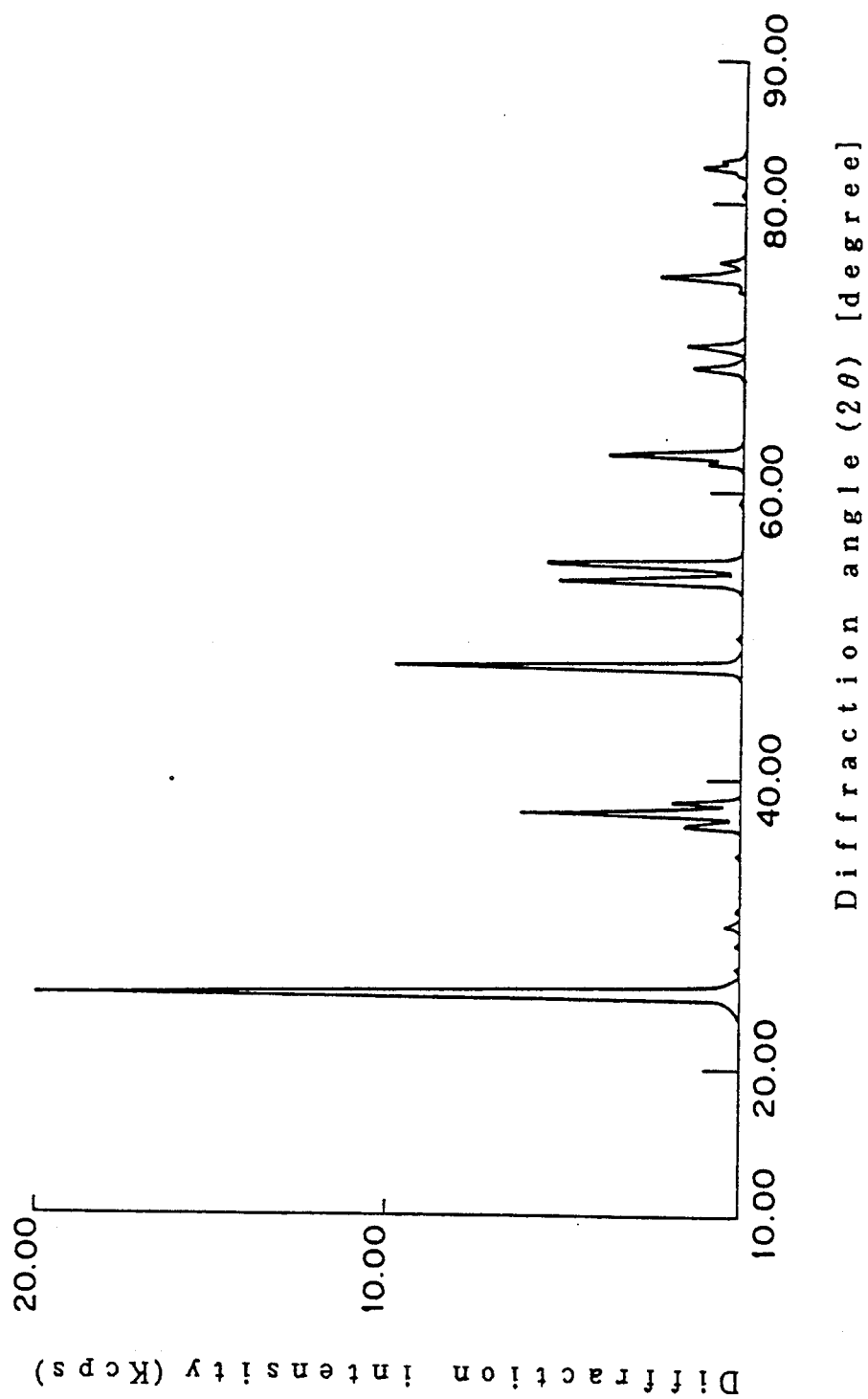
FIG. 1 is a chart showing the result from X-ray diffraction analysis of the catalyst E obtained from the example 2 in the region of a 10° to 90° diffraction angle.

Hereinafter, the present invention is illustrated by the following Examples of some preferred embodiments in comparison with Comparative examples.

EXAMPLE 1

Preparation of catalyst

After mixing 80% concentrated sulfuric acid with ilmenite and carrying out sufficient reaction, an aqueous solution of titanium sulfate was obtained by dilution with water. Iron pieces as reducing agent were added to this, and the iron content from the ilmenite was reduced to ferrous ions; after cooling, ferrous sulfate was precipitated and separated. Into the obtained aqueous solution of titanium sulfate, steam heated to 150° C. was blown, and hydrous titanium oxide was settled. It was washed with water, pickled and washed again with water, and was calcined at 800° C. for 4 hours in a passing air flow. It was crushed by jet air stream to obtain anatase type titanium dioxide (hereinafter, sometimes called simply titanium oxide) with an average particle size of about 0.5 μm and specific surface area of 22 m²/g.

In 6,400 cc of deionized water, 200 g of oxalic acid was dissolved, and 47.24 g of ammonium metavanadate, 5.95 g of ammonium dihydrogen phosphate, 18.67 g of niobium chloride, 8.25 g of cesium sulfate, and 45.91 g of antimony pentoxide (average particle size: 20 μm) were added and stirred. To the obtained solution, 1,800 g of titanium oxide was added, and was stirred by emulsifying machine to prepare a catalyst slurry.

In a stainless steel rotary furnace of 35 cm diameter and 80 cm length which can be heated from outside, 2,000 cc of SiC self-sintered carrier of spherical form with diameter of 6 mm and apparent porosity of 35% was charged, and while rotating the furnace preheated to 200° to 250° C., the slurry was sprayed onto the carrier; the catalytic active substance was thus supported at a rate of 8 g per 100 cc carrier. Afterwards, in passing air, it was calcined in an electric oven for 6 hours at 580° C., to prepare catalyst A.

Table 1 shows the composition of catalyst A, the ratio in the catalytic active substance layer (% by volume) of the pore volume occupied by pores of 0.15 to 0.45 μm diameter to the total fine pore volume occupied by pores of 10 μm or less diameter, and the average particle size and specific surface area of the titanium oxide used in preparation of the catalyst (these are collectively called as catalyst characteristics, hereinafter). The ratio of the pore volume occupied by pores of 0.15 to 0.45 μm diameter to the total fine pore volume is determined from the pore distribution measured by a mercury injection porosimeter.

Catalyst B was prepared as for catalyst A, except that the content of ammonium dihydrogen phosphate was 23.82 g. The catalyst characteristics of catalyst B are shown in Table 1. The phosphorus content in catalyst B was higher than that in catalyst A, and the activity of catalyst B was higher than that of catalyst A.

Oxidation Reaction

Into an iron reaction tube of 25 mm inside diameter and 3 m length immersed in a molten salt bath kept at 390° C., catalyst B was charged as second stage catalyst to a height of 1 m at the material gas outlet end, then catalyst A as first stage catalyst was charged to a height of 1.5 m at the inlet.

o-Xylene was mixed at a ratio of 85 g/Nm³ (synthetic gas) with synthetic gas comprising 10% by volume of oxygen, 10% by volume of steam and 80% by volume of nitrogen, and this mixture was led into the upper inlet of the reaction tube at a space velocity (SV) of 2,500 hr⁻¹ (STP) to oxidize the o-xylene.

At the beginning of reaction and 3 months after start of reaction, the yield of phthalic anhydride was measured, and the results are shown in Table 2. The conversion rate of o-xylene is nearly 100%, and this yield can be regarded as the selectivity to phthalic anhydride.

Comparative example 1

Catalyst C and catalyst D were prepared as in Example 1 (preparation of catalyst) except that 36.73 g of antimony trioxide was used instead of 45.91 g of antimony pentoxide and the addition amount of cesium sulfate was 10.61 g; the oxidation reaction was conducted as in Example 1 (oxidation reaction). The catalyst characteristics of catalysts C and D are shown in Table 1 and results from oxidation reaction in Table 2.

EXAMPLE 2

Catalyst E and catalyst F were prepared as in Example 1 (preparation of catalyst) except that 5.38 g of silver nitrate was also added and the addition amount of cesium sulfate was 5.90 g; the oxidation reaction was conducted as in Example 1 (oxidation reaction). The catalyst characteristics of catalysts E and F are shown in Table 1 and results from oxidation reaction in Table 2.

Comparative example 2

Catalyst G and catalyst H were prepared as in Example 1 (preparation of catalyst) except that 5.38 g of silver nitrate was also added and 36.73 g of antimony trioxide was used instead of 45.91 g of antimony pentoxide; the oxidation reaction was conducted as in Example 1 (oxidation reaction). The catalyst characteristics of catalysts G and H are shown in Table 1 and results from oxidation reaction in Table 2.

With respective to the catalysts E and G which were, respectively, obtained from the example 2 and comparative example 2, difference between the crystal structures of antimony in the catalysts was examined by X-ray diffraction analysis (XRD) using Cu-Kα.

Figure 2:
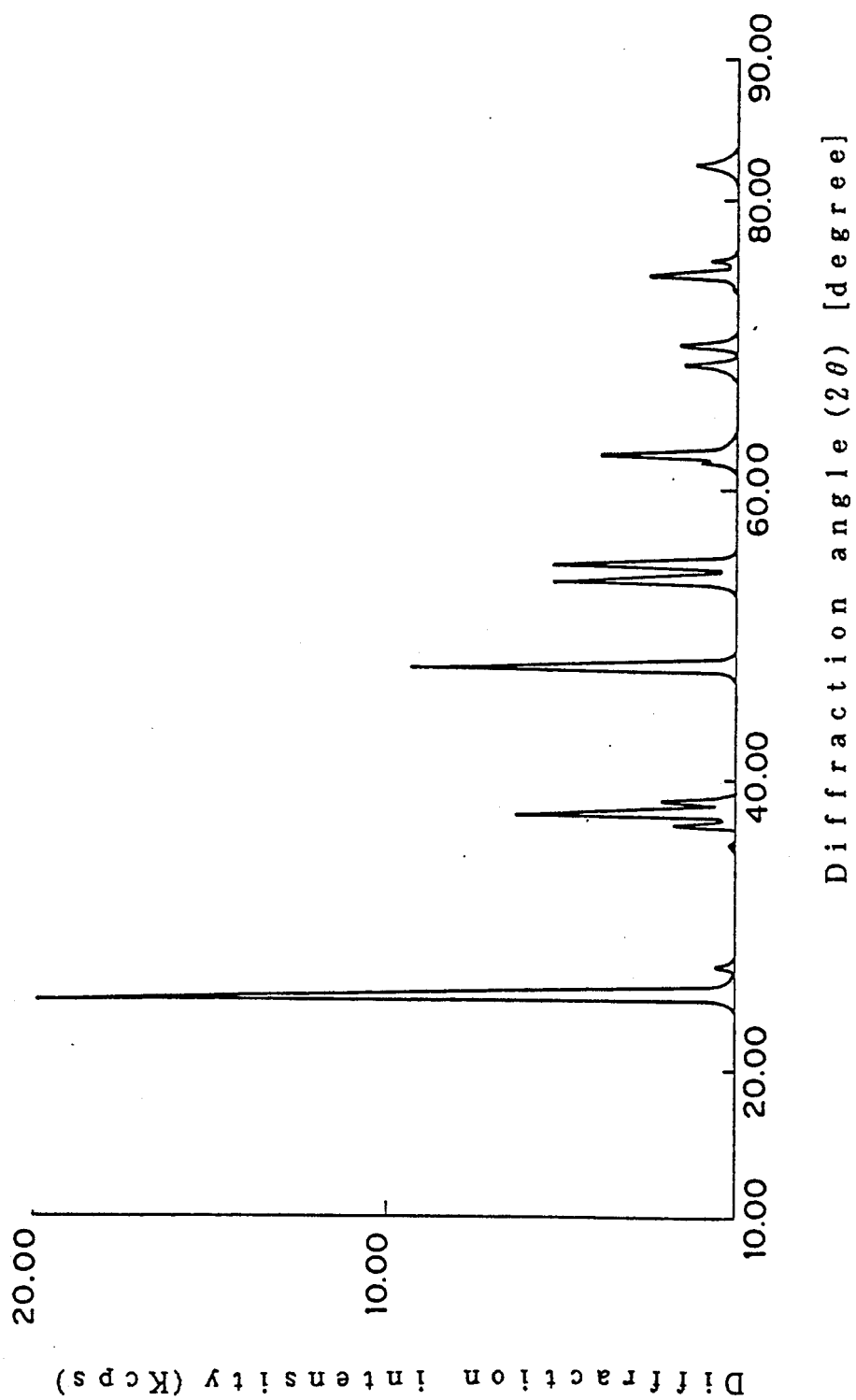
FIG. 2 is a chart showing the result from X-ray diffraction analysis of the catalyst G obtained from the comparative example 2 in the region of a 10° to 90° diffraction angle.

A main component in both catalysts E and G is anatase type $TiO_2$ and, as seen in both FIGS. 1 and 2, large peaks due to the anatase type $TiO_2$ were detected in X-ray diffraction analyses of the catalysts E and G.

Therefore, in order to investigate the difference between five-valent antimony and three-valent antimony, the measurement was carried out with a raised detection sensitivity in a region where a peak due to the anatase type $TiO_2$ is absent (the diffraction angle $2\theta$ is in a range of from 26° to 36°). In Table 3, are shown the peak positions (diffraction angle $2\theta$) of X-ray diffraction analyses in this region due to the antimony compounds having the five-valent and three-valent as well as due to $V_2O_5$ and $Ag_2O$. Meanwhile, the numeral values in parentheses in Table 3 represents relative intensities of the peaks.

Figure 3:
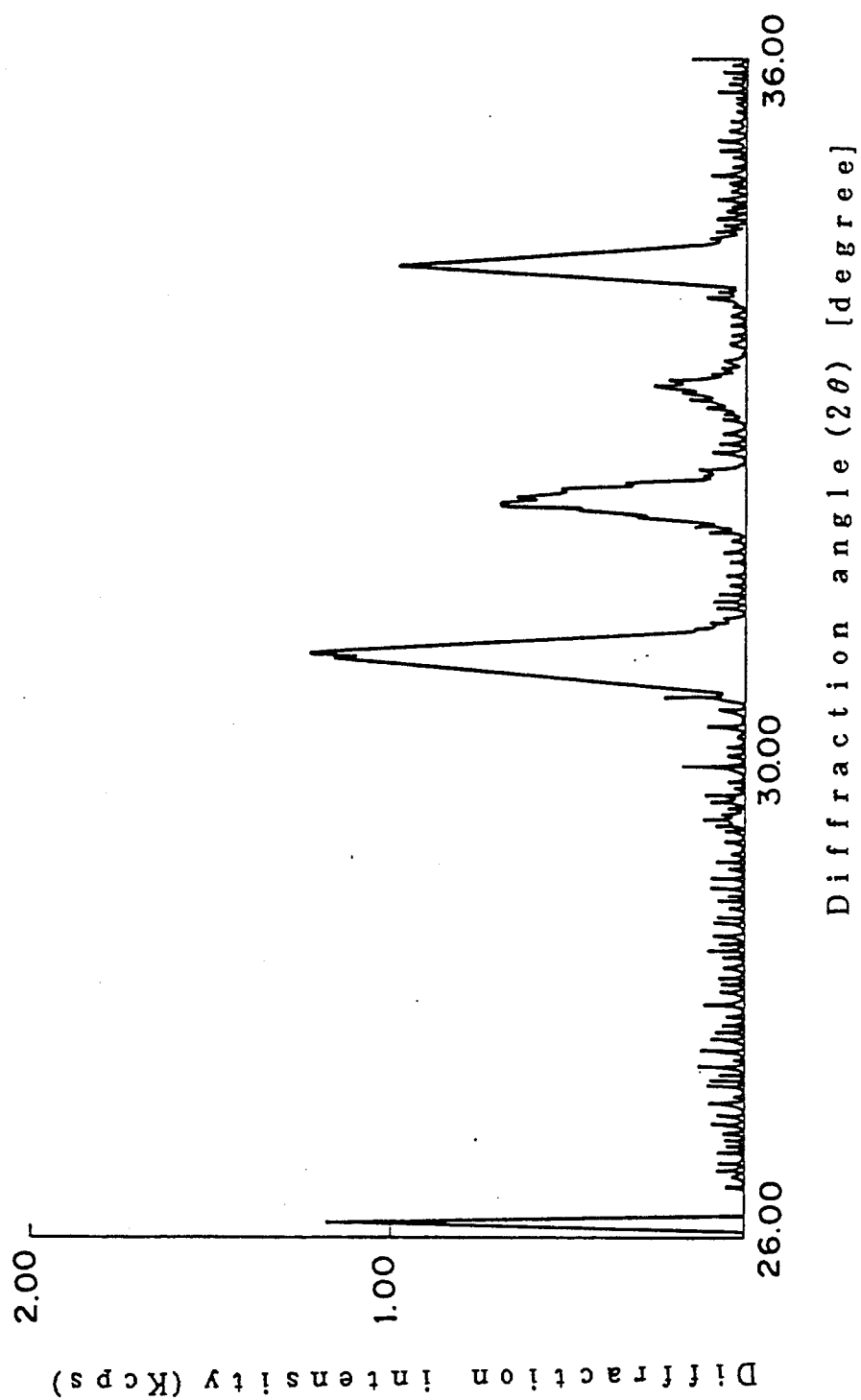
FIG. 3 is a chart showing the result from X-ray diffraction analysis of a catalyst composed of only vanadium and titanium in the region of a 26° to 36° diffraction angle.

For comparison, a catalyst composed of only vanadium and titanium was prepared and, when measurement was carried out in the region where the diffraction angle $2\theta$ is in a range of from 26° to 36°, only a peak due to vanadium pentoxide ($V_2O_5$) was observed as seen in FIG. 3.

Figure 4:
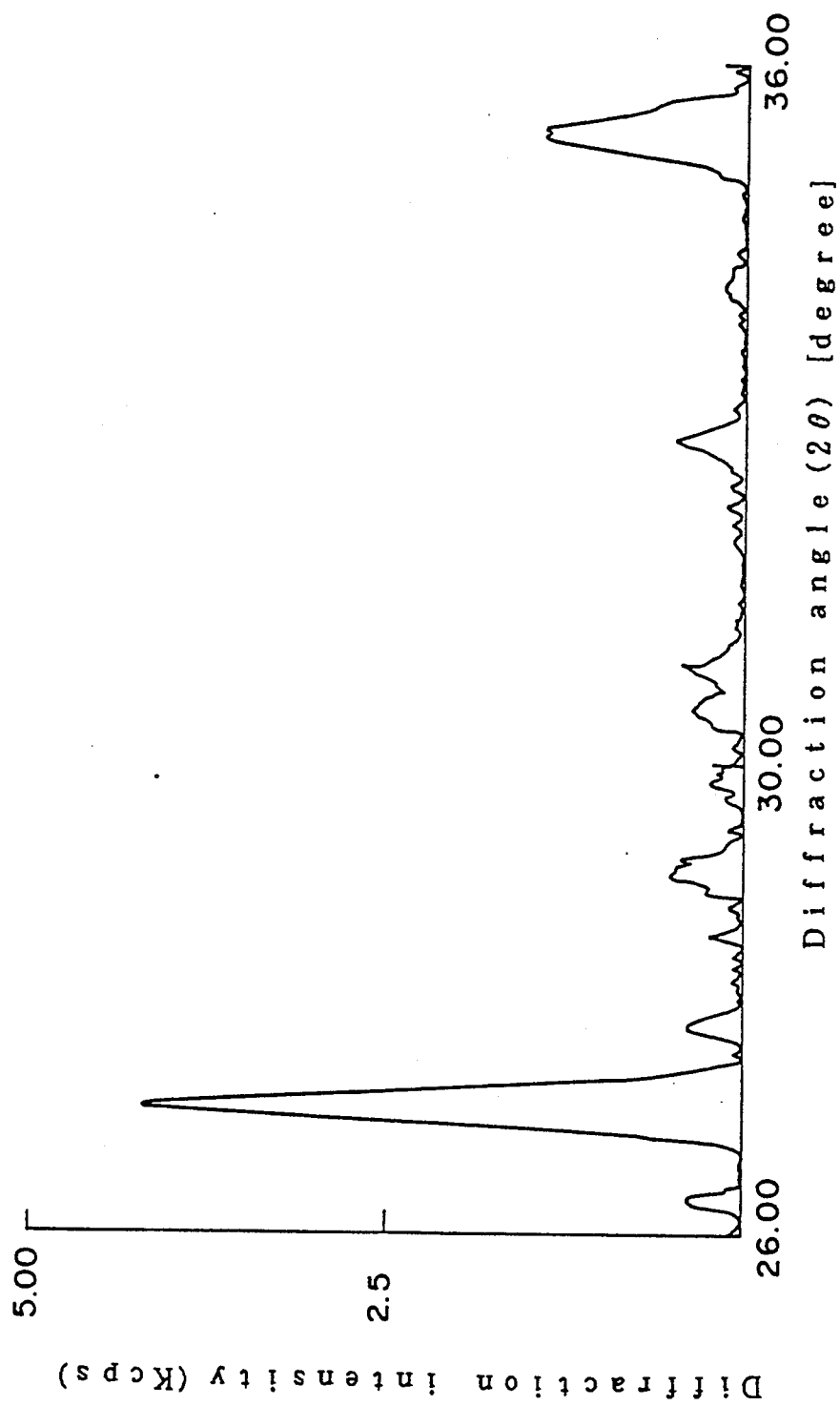
FIG. 4 is a chart showing the result from X-ray diffraction analysis of the catalyst G obtained from the comparative example 2 in the region of a 26° to 36° diffraction angle.

As seen in FIG. 4, in the catalyst G in which antimony trioxide ($Sb_2O_3$) was used, a large peak appeared at $2\theta=27.1°$ and another peak appeared at $2\theta=35.4°$. From these facts and the data in Table 3, antimony is thought to exist in a state near the form of $Sb_2O_4$.

As seen in FIG. 5, in the catalyst E in which antimony pentoxide ($Sb_2O_5$) was used, a large peak appeared at $2\theta=29.9°$ and other peaks appeared at $2\theta=28.6°$ and 34.7°. From these facts and the data in Table 3, antimony is thought to exist in a state near the form of $Sb_6O_{13}$. However, there remain the peaks due to $Sb_2O_5$ at $2\theta=27.1°$, 28.9° and 34.3°.

From the forementioned, the effect of using a five-valent antimony-containing compound as a antimony source may be thought to be due to $Sb_6O_{13}$, but if there is used $Sb_6O_{13}$ which was led from $Sb_2O_5$ by calcining it beforehand at a temperature of 700° (no change in the surface area), the effect of present invention is not attained and a catalyst of high activity for a low temperature reaction is only obtained.

EXAMPLE 3

Ilmenite and 80% concentrated sulfuric acid were mixed and allowed to react sufficiently, then the product was diluted with water to obtain an aqueous solution of titanium sulfate. Iron pieces were added as reducing agent, and the iron content from the ilmenite was reduced to ferrous ions; after cooling, ferrous sulfate was precipitated and separated. Into the obtained aqueous solution of titanium sulfate, steam heated to 150° C. was blown, and hydrous titanium oxide was settled. It was washed with water, pickled, and washed again with water, and was calcined at 700° C. for 4 hours in a passing air flow. It was crushed by jet air stream, and anatase type titanium dioxide with specific surface area of 33 $m^2/g$ measured by the BET method and average particle size of about 0.45 μm was obtained.

In 6,400 cc of deionized water, 900 g of oxalic acid was dissolved, and to this aqueous solution, 408.50 g of ammonium metavanadate, 10.30 g of ammonium dihydrogen phosphate, 17.22 g of niobium chloride, 4.08 g of cesium sulfate, 3.92 g of potassium sulfate, and 52.93 g of antimony pentoxide (average particle size: 20 μm) were added and sufficiently stirred. To the obtained solution, 1,800 g of titanium oxide (which was the above-obtained anatase type titanium dioxide) was added, and the mixture was stirred by emulsifying machine to prepare a catalyst slurry.

Using this slurry, the catalytic active substance was supported as in Example 1 at a supporting rate of 8.0 g per 100 cc of carrier, followed by calcining in passing air in an electric oven at 560° C. for 6 hours to prepare catalyst I.

Catalyst J was prepared as for catalyst I, except that the amount for use of ammonium dihydrogen phosphate was 30.89 g.

Oxidation reaction

Into an iron reaction tube of 25 mm inside diameter and 3 m length immersed in a molten salt bath kept at 395° C., catalyst J was charged as second stage catalyst to a height of 1 m, then catalyst I as first stage catalyst to a height of 1.5 m; naphthalene which was mixed at a ratio of 85 g/$Nm^3$ (synthetic gas) with synthetic gas comprising 10% by volume of oxygen, 10% by volume of steam and 80% by volume of nitrogen was introduced into the upper part of the reaction tube at a space velocity of 2,500 $hr^{-1}$ (STP) to perform the oxidation. Results are shown in Table 2.

Comparative example 3

Catalyst K and catalyst L were prepared as for catalysts I and J in Example 3 (preparation of catalyst), except that 42.34 g of antimony trioxide was used instead of 52.93 g of antimony pentoxide and the addition amount of cesium sulfate was 5.44 g; the oxidation reaction was performed as in Example 3 (oxidation reaction). The catalyst characteristics of catalysts K and L are shown in Table 1 and results from oxidation reaction in Table 2.

EXAMPLE 4

Catalyst M and catalyst N were prepared as in Example 3 (preparation of catalyst), except that 31.04 g of silver nitrate was also added and the addition amount of cesium sulfate was 2.72 g; the oxidation reaction was performed as in Example 1 (oxidation reaction). The catalyst characteristics of catalysts M and N are shown in Table 1 and results from oxidation reaction in Table 2.

Comparative example 4

Catalyst O and catalyst P were prepared as in Example 3 (preparation of catalyst), except that 31.04 g of silver nitrate was also added and 42.34 g of antimony trioxide was used instead of 52.93 g of antimony pentoxide; the oxidation reaction was performed as in Example 1 (oxidation reaction). The catalyst characteristics of catalysts O and P are shown in Table 1 and results from oxidation reaction in Table 2.

TABLE 1

| | | Composition of catalyst (ratio by weight) | | | | | | | | Titanium oxide | | Pore volume ratio |
| | Catalyst | $V_2O_5$ | $TiO_2$ | $Nb_2O_5$ | $P_2O_5$ | $Cs_2O$ | $Ag_2O$ | $Sb_2O_5$ | $Sb_2O_3$ | $K_2O$ | Average particle size | Specific surface area | |
|---|---|---|---|---|---|---|---|---|---|---|---|---|---|
| Example 1 | A | 2 | 98 | 0.5 | 0.2 | 0.35 | — | 2.5 | — | — | 0.5 | 22 | 86 |
| | B | 2 | 98 | 0.5 | 0.8 | 0.35 | — | 2.5 | — | — | " | " | 87 |
| Comparative example 1 | C | 2 | 98 | 0.5 | 0.2 | 0.45 | — | — | 2.0 | — | " | " | 86 |
| | D | 2 | 98 | 0.5 | 0.8 | 0.45 | — | — | 2.0 | — | " | " | 87 |
| Example 2 | E | 2 | 98 | 0.5 | 0.2 | 0.25 | 0.2 | 2.5 | — | — | " | " | 86 |
| | F | 2 | 98 | 0.5 | 0.8 | 0.25 | 0.2 | 2.5 | — | — | " | " | 87 |
| Comparative example 2 | G | 2 | 98 | 0.5 | 0.2 | 0.35 | 0.2 | — | 2.0 | — | " | " | 86 |
| | H | 2 | 98 | 0.5 | 0.8 | 0.35 | 0.2 | — | 2.0 | — | " | " | 87 |
| Example 3 | I | 15 | 85 | 0.4 | 0.3 | 0.15 | — | 2.5 | — | 0.1 | 0.45 | 33 | 80 |
| | J | 15 | 85 | 0.4 | 0.9 | 0.15 | — | 2.5 | — | 0.1 | " | " | 81 |
| Comparative example 3 | K | 15 | 85 | 0.4 | 0.3 | 0.20 | — | — | 2.0 | 0.1 | " | " | 80 |
| | L | 15 | 85 | 0.4 | 0.9 | 0.20 | — | — | 2.0 | 0.1 | " | " | 81 |

TABLE 1-continued

| | Catalyst | Composition of catalyst (ratio by weight) | | | | | | | | | Titanium oxide | | Pore volume ratio |
| --- | --- | --- | --- | --- | --- | --- | --- | --- | --- | --- | --- | --- | --- |
| | | $V_2O_5$ | $TiO_2$ | $Nb_2O_5$ | $P_2O_5$ | $Cs_2O$ | $Ag_2O$ | $Sb_2O_5$ | $Sb_2O_3$ | $K_2O$ | Average particle size | Specific surface area | |
| Example 4 | M | 15 | 85 | 0.4 | 0.3 | 0.10 | 1.0 | 2.5 | — | 0.1 | " | " | 80 |
| | N | 15 | 85 | 0.4 | 0.9 | 0.10 | 1.0 | 2.5 | — | 0.1 | " | " | 81 |
| Comparative example 4 | O | 15 | 85 | 0.4 | 0.3 | 0.15 | 1.0 | — | 2.0 | 0.1 | " | " | 80 |
| | P | 15 | 85 | 0.4 | 0.9 | 0.15 | 1.0 | — | 2.0. | 0.1 | " | " | 81 |

Average particle size: μm
Specific surface area: m²/g
Pore volume ratio (Ratio of pore volume occupied by pores of 0.15 to 0.45 μm diameter to the total fine pore volume occupied by pores of 10 μm or less diameter): % by volume

TABLE 2

| Catalyst | | Yield of phthalic anhydride (% by weight) | |
| --- | --- | --- | --- |
| First stage | Second stage | Initial (*) | After 3 months (*) |
| Example 1 A | B | 112.5 (392) | 112.7 (390) |
| Comparative example 1 C | D | 109.8 (392) | 110.1 (389) |
| Example 2 E | F | 113.8 (392) | 114.0 (391) |
| Comparative example 2 G | H | 111.7 (390) | 112.0 (387) |
| Example 3 I | J | 102.0 (394) | 102.2 (388) |
| Comparative example 3 K | L | 99.8 (392) | 100.0 (387) |
| Example 4 M | N | 103.9 (394) | 104.2 (388) |
| Comparative example 4 O | P | 102.0 (392) | 102.3 (387) |

(*) Molten salt temperature
Examples 1 and 2 and Comparative examples 1 and 2: o-xylene → phthalic anhydride
Examples 3 and 4 and Comparative examples 3 and 4: napthalene → phthalic anhydride

TABLE 3

| $V_2O_5$ | $Sb_2O_3$ | $Sb_2O_4$ |
| --- | --- | --- |
| 26.2° (90) | 27.7° (100) | 27.4° (100) |
| 31.0° (65) | 32.1° (40) | 35.0° (70) |
| 32.4° (35) | 35.0° (11) | |
| 33.3° (16) | | |
| 34.3° (40) | | |
| 36.0° (8) | | |

| $Sb_2O_5$ | $Sb_6O_{13}$ | $Ag_2O$ |
| --- | --- | --- |
| 27.2° (90) | 28.6° (20) | 32.7° (100) |
| 29.0° (80) | 29.9° (100) | |
| 30.5° (80) | 34.7° (30) | |
| 33.6° (40) | | |
| 34.0° (80) | | |

What is claimed are:

1. A catalyst for producing phthalic anhydride by vapor phase catalytic oxidation of o-xylene and/or naphthalene with molecular oxygen or gas containing molecular oxygen, having supported on a heat-resistant inorganic carrier a catalytic active substance comprising (A) 1 to 20 parts by weight of vanadium oxide as $V_2O_5$ and 99 to 80 parts by weight of anatase type titanium dioxide with specific surface area of 10 to 60 m²/g as $TiO_2$ and (B), per 100 parts by total weight of (A), 0.01 to 1 part by weight of niobium as $Nb_2O_5$, 0.05 to 2 parts by weight of at least one element selected from potassium, cesium, rubidium and thallium as oxide, 0.2 to 1.2 parts by weight of phosphorus as $P_2O_5$, and 0.55 to 5.5 parts by weight as $Sb_2O_5$ of antimony obtained by using a five-valent antimony compound as an antimony source.

2. A catalyst for producing phthalic anhydride by vapor phase catalytic oxidation of o-xylene and/or naphthalene with molecular oxygen or gas containing molecular oxygen, having supported on a heat-resistant inorganic carrier a catalytic active substance comprising (A) 1 to 20 parts by weight of vanadium oxide as $V_2O_5$ and 99 to 80 parts by weight of anatase type titanium dioxide with specific surface area of 10 to 60 m²/g as $TiO_2$ and (C), per 100 parts by total weight of (A), 0.01 to 1 part by weight of niobium as $Nb_2O_5$, 0.05 to 2 parts by weight of at least one element selected from potassium, cesium, rubidium and thallium as oxide, 0.2 to 1.2 parts by weight of phosphorus as $P_2O_5$, 0.05 to 2 parts by weight of silver as $Ag_2O$, and 0.55 to 5.5 parts by weight as $Sb_2O_5$ of antimony obtained by using a five-valent antimony compound as an antimony source.

3. A catalyst for producing phthalic anhydride according to claim 1 wherein, in the catalytic active substance layer supported on the heat-resistant inorganic carrier, the pore volume occupied by pores of 0.15 to 0.45 μm diameter is 50% or more of the total fine pore volume occupied by pores of 10 μm or less diameter.

4. A process for producing phthalic anhydride by passing o-xylene and/or naphthalene together with molecular oxygen or gas containing molecular oxygen through a catalyst layer;
   wherein said catalyst layer in a reaction tube is divided into two or more sections to make a plurality of reaction zones, and a plural piece of catalysts of controlled activity are charged in the zones so that the catalytic activity is higher from the material gas inlet of the reaction tube toward the outlet; and
   wherein said catalyst has, supported on a heat-resistant inorganic carrier, a catalytic active substance comprising (A) 1 to 20 parts by weight of vanadium oxide as $V_2O_5$ and 99 to 80 parts by weight of anatase type titanium dioxide with specific surface area of 10 to 60 m²/g as $TiO_2$ and (B), per 100 parts by total weight of (A), 0.01 to 1 part by weight of niobium as $Nb_2O_5$, 0.05 to 2 parts by weight of at least one element selected from potassium, cesium, rubidium and thallium as oxide, 0.2 to 1.2 parts by weight of phosphorus as $P_2O_5$, and 0.55 to 5.5 parts by weight as $Sb_2O_5$ of antimony obtained by using a five-valent antimony compound as an antimony source.

5. A process for producing phthalic anhydride by passing o-xylene and/or naphthalene together with molecular oxygen or gas containing molecular oxygen through a catalyst layer;
   wherein said catalyst layer in a reaction tube is divided into two or more sections to make a plurality of reaction zones, and a plural piece of catalysts of controlled activity are charged in the zones so that the catalytic activity is higher from the material gas inlet of the reaction tube toward the outlet;

wherein said catalyst has, supported on a heat-resistant inorganic carrier, a catalytic active substance comprising (A) 1 to 20 parts by weight of vanadium oxide as $V_2O_5$ and 99 to 80 parts by weight of anatase type titanium dioxide with specific surface area of 10 to 60 $m^2/g$ as $TiO_2$ and (C), per 100 parts by total weight of (A), 0.01 to 1 part by weight of niobium as $Nb_2O_5$, 0.05 to 2 parts by weight of at least one element selected from potassium, cesium, rubidium and thallium as oxide, 0.2 to 1.2 parts by weight of phosphorus as $P_2O_5$, 0.05 to 2 parts by weight of silver as $Ag_2O$, and 0.55 to 5.5 parts by weight as $Sb_2O_5$ of antimony obtained by using a five-valent antimony compound as an antimony source.

* * * * *